(12) United States Patent
Cheon et al.

(10) Patent No.: US 6,783,569 B2
(45) Date of Patent: Aug. 31, 2004

(54) METHOD FOR SYNTHESIS OF CORE-SHELL TYPE AND SOLID SOLUTION ALLOY TYPE METALLIC NANOPARTICLES VIA TRANSMETALATION REACTIONS AND APPLICATIONS OF SAME

(75) Inventors: Jin Woo Cheon, Taejeon (KR); Jong Il Park, Kyungsangbuk-do (KR)

(73) Assignee: Korea Advanced Institute of Science and Technology, Taejeon (KR)

( * ) Notice: Subject to any disclaimer, the term of this patent is extended or adjusted under 35 U.S.C. 154(b) by 29 days.

(21) Appl. No.: 09/991,464

(22) Filed: Nov. 21, 2001

(65) Prior Publication Data

US 2003/0039860 A1 Feb. 27, 2003

(30) Foreign Application Priority Data

Aug. 16, 2001 (KR) .................................... 2001-0049385

(51) Int. Cl.[7] .................................................. B22F 9/16
(52) U.S. Cl. .............................. 75/348; 75/351; 75/362; 75/371
(58) Field of Search .......................... 75/348, 351, 362, 75/371, 372

(56) References Cited

U.S. PATENT DOCUMENTS

| | | | | |
|---|---|---|---|---|
| 5,876,480 A | * | 3/1999 | Markowitz et al. ............ | 75/252 |
| 6,103,868 A | * | 8/2000 | Heath et al. ................. | 528/482 |
| 6,254,662 B1 | * | 7/2001 | Murray et al. ................ | 73/348 |
| 6,436,167 B1 | * | 8/2002 | Chow et al. ................... | 73/371 |
| 2003/0140731 A1 | * | 7/2003 | Bocarsly et al. .............. | 75/370 |

* cited by examiner

Primary Examiner—George Wyszomierski
(74) Attorney, Agent, or Firm—Perkins Coie LLP; Paul L. Hickman; David B. Dort

(57) ABSTRACT

Disclosed is a method for producing core-shell type metallic nanoparticles involving (i) providing a dispersion of a first metal as nanoparticles in an appropriate organic solvent; (ii) providing a solution of a metallic precursor containing a second metal in an appropriate organic solvent, in which the second metal has a reduction potential higher than that of the first metal; and (iii) combining the dispersion from (i) and the solution from (ii) together to carry out the transmetalation reaction of the first and second metals, thereby forming core-shell type metallic nanoparticles.

7 Claims, 10 Drawing Sheets

Core-shell type cobalt-platinum nanoparticles / MMPc

FIG. 14A
300 K
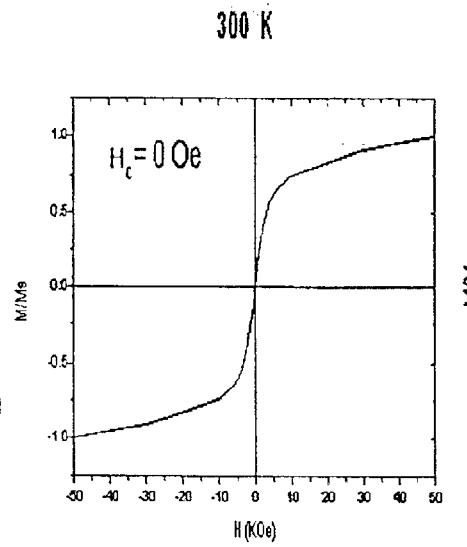
Core-shell type cobalt-platinum nanoparticles
↓ 700 °C 12 hr Thermal treatment
$Co_1Pt_1$
Solid solution alloy type cobalt-platinum nanoparticles
FIG. 14B
5 K
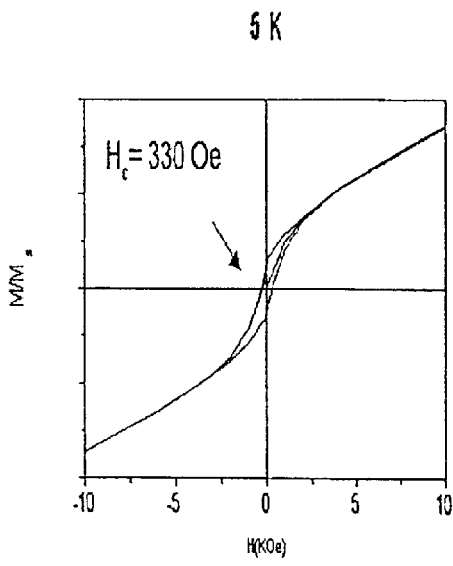
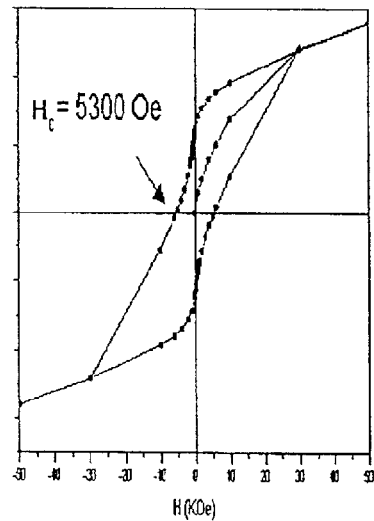
FIG 14C
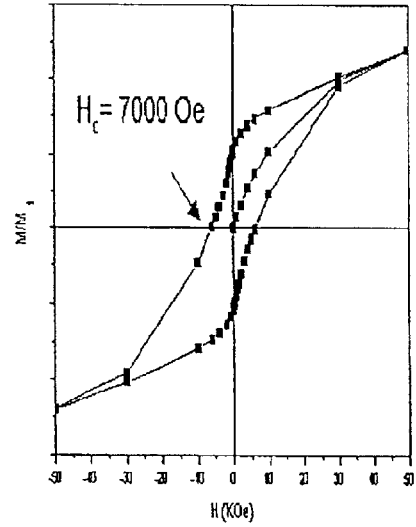
FIG 14D

METHOD FOR SYNTHESIS OF CORE-SHELL TYPE AND SOLID SOLUTION ALLOY TYPE METALLIC NANOPARTICLES VIA TRANSMETALATION REACTIONS AND APPLICATIONS OF SAME

CROSS REFERENCE TO PRIORITY DOCUMENTS

This application claims priority under 35 U.S.C. 119(a-d) and 35 U.S.C. 120 to Korean Patent Application 2001-0049385 filed in the Korean Intellectual Property Office on Aug. 16, 2001, and which is incorporated by reference herein in its entirety.

FIELD OF THE INVENTION

The present invention relates to a method for synthesis of core-shell type and solid solution alloy type metallic nanoparticles via transmetalation reactions and their applications. More particularly, the present invention relates to a method for synthesis of core-shell type and solid solution alloy type metallic nanoparticles (including rod shape, hereinafter referred to as "nanoparticles") in which the particles have a size of 1 to 100 nm and comprise two or more metals.

DESCRIPTION OF THE RELATED ART

The term nanoparticles denotes particles whose size is from 1 to 100 nm and having characteristic optical, electrical, magnetic and catalytic properties different from the same bulk matter, due to their quantum effect and large surface area. For this reason, currently, there is much effort being made to develop a synthesis method of such nanoparticles. In spite of such efforts, however, the synthesis methods developed up to now are still far from perfect. Metallic alloy nanoparticles may compensate for the defects of single element nanoparticles, such as tendency to be readily oxidized, corrosiveness, and deterioration of chemical-physical properties. Also, they may exhibit enhanced catalytic effects in chemical reactions. In case of using magnetic metals, the resulting nanoparticles may have increased coercive force by increase of magnetic anisotropy. Further, it is possible to use the alloy nanoparticles as materials for magnetic recording media since they are stable in the air to not undergo oxidation.

So far, most alloy structures have been achieved by using a physical vacuum vapor deposition method to form a thin layer. Research and studies on such vacuum vapor deposition method have been conducted. However, the above method has disadvantages such as chaotic growth of particles and non-uniformity of particle size thereby causing deterioration of properties of the particles.

Recently, Sun et al. have developed a novel synthesis method for forming a thin layer of nanoparticles with improved properties (see, Science-2000, 287, 1989).

As methods using chemical synthesis methods, it has been reported that cobalt-platinum and iron-platinum alloy nanoparticles are prepared by reducing metallic ions or organo-metallic compounds to metals using chemical reducing agents such as hydrides for example, $NaBH_4$, $NaBEt_3H$, and $N_2H_4$ (see, for example, Science. 2000, 287, 1989; J. Appl. Phys. 2000, 87, 5615; J. Phys. Chem. B 2000, 104, 695; and J. Appl. Phys. 1999, 85, 5184). Also, Sun et al. at IBM have tried to apply cobalt nanoparticles produced via chemical reduction with a hydride or diol to single electron devices.

Similarly, with respect to gold-silver, copper-silver, copper-palladium, palladium-platinum, palladium-gold and copper-platinum alloy nanoparticles, production methods by reduction using hydride or alcohol as a reducing agent also have been described (see, for example, J. Phys. Chem. 1992, 96, 9730; J. Phys. Chem. 1997, 101, 5301; J. Phys. Chem. 1991, 96, 7448; Langmuir, 1995, 11, 693; Chem. Mater. 1993, 5, 254; Chem. Mater. 1996, 8, 1895; Langmuir, 1994, 10, 4574; Langmuir 1993, 9, 1664; J. Phys. Chem. 1992, 96, 9927; and J. Phys. Chem. B 1997, 101, 7033).

Such noble metallic nanoparticles can be used as reducing catalysts in the reduction of double bonds in organic compounds such as olefin. This is because the reduction in size of particles to nanometer level leads to an increase of surface area and thereby, activity level.

As discussed above, there have been made numerous efforts to find, a method for synthesizing nanoparticles consisting of heterogeneous elements. However, it is not secured that nanoparticles produced by the method described in the above-listed studies have a uniform particle size, and composition ratio of the nanoparticles cannot be stably controlled. Therefore, there are problems in their utility for actual industries, as well as in preparing core-shell type nanoparticles themselves.

SUMMARY OF THE INVENTION

The present inventors have studied to overcome the several problems occurring in the prior art and to develop a novel method for synthesizing core-shell type and solid solution alloy type metallic nanoparticles. As a result, they have accomplished a novel method for synthesizing core-shell type and solid solution alloy type metallic nanoparticles by only a metallic transmetalation reaction taking advantage of oxidation-reduction potential differences between heterogeneous metals, without any additional catalyst. This forms the present invention.

The transmetalation reaction between two metals according to the present invention occurs due to the redox potential difference between them. That is, because of the potential difference between two metals, when they come into contact with each other, one metal atom of 0 charge is oxidized to form an ion and the other ionic metal is reduced to form elemental metal, whereby transmetalation reaction between two metals occurs. Reactivity of such substitution reaction can be predicted in accordance with the ionization tendencies of the reactant metals.

Therefore, the object of the present invention is to provide a method for producing core-shell type metallic nanoparticles having a stable and uniform particle size, or solid solution alloy type metallic nanoparticles having a certain composition ratio, via transmetalation reactions of various metals without any additional reducing agent, on the basis of the ionization tendencies of the substituent metals.

Another object of the present invention is to provide applications in various industrial fields, including information recording media, catalysts, medical treatment agents, etc., using the metallic alloy nanoparticles produced according to the present invention.

Thus, in the first aspect of the present invention, there is provided a method for producing core-shell type metallic nanoparticles comprising (i) providing a dispersion of a first metal as nanoparticles in an appropriate organic solvent; (ii) providing a solution of a metallic precursor containing a second metal in an appropriate organic solvent, in which the second metal has a reduction potential higher than that of the first metal; and (iii) combining the dispersion from (i) and the solution from (ii) together to carry out the transmetalation reaction of the first and second metals, thereby forming core-shell type metallic nanoparticles.

In the second aspect according to the present invention, there is provided a method for producing solid solution alloy type metallic nanoparticles comprising (i) providing a solution of a thermally degradable metallic precursor containing a first metal in an appropriate organic solvent; (ii) providing a solution of a metallic precursor containing a second metal in an appropriate organic solvent, in which the second metal has a reduction potential higher than that of the first metal; and (iii) combining the solutions from (i) and (ii) together to carry out the transmetalation reaction of the first and second metals, thereby forming solid solution alloy type metallic nanoparticles

BRIEF DESCRIPTION OF THE DRAWINGS

The above objects, and other features and advantages of the present invention will become more apparent after a reading of the following detailed description when taken in conjunction with the drawings, in which:

FIGS. 14a–14d shows magnetic hysteresis loops of core-shell type cobalt-platinum nanoparticles produced according to the present invention, which are spin-coated on a silicone substrate before and after a thermal treatment;

DETAILED DESCRIPTION OF THE INVENTION

Figure 1:
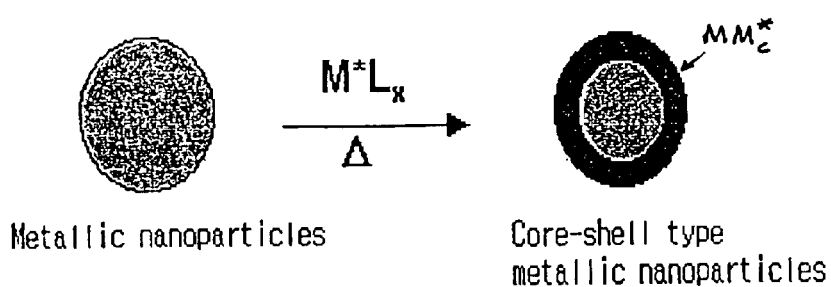
FIGS. 1 and 2 show diagrams illustrating syntheses of a core-shell type and a solid solution alloy type metallic nanoparticle, respectively.

The present invention is described in detail below.

According to the first aspect of the present invention, the present invention relates to a method for producing core-shell type metallic nanoparticles comprising (i) providing a dispersion a first metal as nanoparticles in an appropriate organic solvent; (ii) dissolving a metallic precursor containing a second metal in an appropriate organic solvent, in which the second metal has a reduction potential higher than that of the first metal; and (iii) combining solutions from (i) and (ii) together to carry out the transmetalation reaction of the first and second metals, thereby forming core-shell type metallic nanoparticles.

The first metal is not required to be limited to a specific metal as long as it has a reduction potential lower than that of the second metal. Preferably, the first metal may comprise a member selected from the group consisting of manganese, chromium, iron, cobalt, nickel, copper, silver, palladium, platinum and gold. The first metal may be prepared into nanoparticles by a known method such as a thermal decomposing method of organic metallic compounds as described later in Example 1, but is not limited thereto. Also, the first metal, other than single element metals, may comprise at least two metals of core-shell type or solid solution alloy type. Specific examples thereof include core-shell type metallic nanoparticles or solid solution alloy type nanoparticles comprising two different metals such as manganese-chromium, manganese-iron, manganese-cobalt, manganese-nickel, manganese-copper, manganese-silver, manganese-palladium, manganese-platinum, manganese-gold, chromium-iron, chromium-cobalt, chromium-nickel, chromium-copper, chromium-silver, chromium-palladium, chromium-platinum, chromium-gold, iron-cobalt, iron-nickel, iron-copper, iron-silver, iron-palladium, iron-platinum, iron-gold, cobalt-nickel, cobalt-copper, cobalt-silver, cobalt-palladium, cobalt-platinum, cobalt-gold, nickel-copper, nickel-silver, nickel-palladium, nickel-platinum, nickel-gold, copper-silver, copper-palladium, copper-platinum, copper-gold, silver-palladium, silver-platinum, silver-gold, palladium-platinum, palladium-gold, platinum-gold, etc; core-shell type metallic nanoparticles or solid solution alloy type nanoparticles comprising three different metals such as iron-cobalt-nickel, chromium-iron-cobalt, manganese-iron-cobalt, chromium-iron-nickel, manganese-iron-nickel, manganese-chromium-iron, chromium-cobalt-nickel, manganese-cobalt-nickel, manganese-chromium-cobalt, manganese-chromium-nickel, etc; and core-shell type metallic nanoparticles or solid solution alloy type nanoparticles comprising multi-metals of more than three kinds.

The second metal used in the present invention is not limited to a specific metal as long as it has a reduction potential higher than that of the first. The reduction potential is associated with the ionization tendency of metals and can be referred to Handbook of Chemistry and Physics, $76^{th}$ ed.; CRC press, 1995, pp 8–21. For example, ionization tendency of metals decreases in the order of K>Ca>Na>Mg>Al>Mn>Zn>Cr>Fe>Co~Ni>Cu>Hg~Ag>Pd~Pt>Au. As positioned toward the left, the metal has a low reduction potential and thereby, a strong tendency to be oxidized. On the other hand, as positioned toward the right end, the metal has a high reduction potential and thereby, a strong tendency to be reduced.

Therefore, if a first metal is given, then a second metal to be transmetalated with the first metal should be selected from the group of consisting of metals having a reduction potential higher than that of the first. Further, it will be understood that when the reduction potential difference is large, the transmetalation reaction will be performed more effectively.

The metallic precursor containing the second metal is not particularly limited as long as it has a suitable composition for transmetalation with the first metal. Examples which satisfy the above requirements comprise at least one member selected from the group consisting of β-diketonate compounds, phospine compounds, organic metallic compounds, hydrocarbonate ammonium salt compounds of $R_4N$, in which R is a straight or branched chain having 1to 22 carbon atoms or a chain containing a phenyl group, and the like. The β-diketonate compounds may include, for example, $Pt(hfac)_2$ (hfac: hexafluoroacetylacetonate), $Au(hfac)$ $(PPh_3)$ ($PPh_3$: triphenylphospine), $Au(hfac(PMe_3)$, $Me_2Au(hfac)$, $Me_2Au(tfac)$ (tfac:trifluoroacetylacetonate), $Pd(hfac)_2$, $Au(acac)$ $(PPh_3)$ (acac: acetylacetonate), $Au(acac)$ $(PMe_3)$, $Ag(hfac)$, $Ag(hfac)$ $(PR_3)$, $Cu(hfac)_2$, $Pt(acac)_2$, $Pd(acac)_2$, $Ag(acac)$, $Ag(acac)$ $(PR_3)$, $Cu(acac)_2$, and the like, in which R is a straight or branched chair, having 1 to 22 carbon atoms or a chain containing a phenyl group, and the like. The phospine compounds may include, for example, $Pt(PR_3)_4$, $AuCl(PPh_3)$, $Pd(PR_3)_4$, $[Ag(PR_3)I]_4$, $AuPR_3Cl$, $[(PR_3)_2]CuNo_3$, and the like, in which R is a straight or branched chain having 1 to 22 carbon atoms or a chain containing a phenyl group, and the like. The organic metallic compounds may include, for example, $Me_3AuPMe_3$, $EtAuPMe_3$, $Pt(COD)Cl_2$ (COD: cyclooctadiene), $Pt(COD)$ $(CH_3)_2$, $Pd(COD)Cl_2$, $Pd(COD)$ $(CH_3)_2$, and the like. The hydrocarbonate ammonium salts $(R_4N)$ may include, for example, $[R_4N]AuCl_4$, $[R_4N]_2PtCl_4$, $[R_4N]_2PdCl_4$. $[R_4N]_2CuCl_4$, and the like, in which R is a straight or branched chain having 1 to 22 carbon atoms or a chain containing a phenyl group, and the like.

Now, the method for producing the core-shell type metallic nanoparticles will be described in detail.

Firstly, as core, nanoparticles of the first metal are dispersed in an appropriate organic solvent to provide a dispersion of the first metal. The nanoparticles of the first metal may comprise a single element metal, or multi-element metals of a core-shell type or a solid solution alloy type, as described above.

Then, as shell, a metallic precursor containing the second metal to be transmetalated with the first metal is dissolved in an appropriate organic solvent to provide a solution of the metallic precursor containing the second metal.

The solvent which can be used to disperse the first metal and to dissolve the metallic precursor containing the second metal is not particularly limited. As specific examples, hexadecane, decane, nonane, dodecane, toluene, anisole, diphenylether, dioctylether, dichlorobenzene, and the like nay be included.

Preferably, upon preparing the solution of the metallic precursor containing the second metal, an appropriate stabilizer may be added to the solution so that the nanoparticles form a stable single dispersion phase in the solution. Examples of the stabilizer suitable for the present invention include compounds having following structures:

R—X in which R is a straight or branched hydrocarbonate group having 2 to 22 carbon atoms and X is selected from a isocyanate group, sulphonate group, phosphate group, carboxylate group, amine group and thiol group.

Finally, the solution of the first metal and the solution of the metallic precursor are combined together to initiate a transmetalation reaction through the oxidation-reduction of the first metal and the second metal. The specific conditions required for the transmetalation reaction, although not particularly limited, include preferably a reaction temperature of 50 to 300° C., more preferably 120 to 150° C. Preferably, the reaction temperature should be maintained for 1 to 12 hours so as to produce a uniform core-shell structure.

Thusly obtained core-shall type metallic nanoparticles are added to an appropriate polar solvent and centrifuged to separate them from the reaction solution. Here, the polar solvent which can be used includes alcohols of short chains, including for example, methanol, ethanol, isopropanol, and the like, but is not limited thereto.

The separated nanoparticles must be redispersed and repeptized in an organic solvent so as to be used in practical industrial fields. Solvents which can be in this case include for example, toluene, hexane, nonane, decane, anisole, tetrahydrofuran, and the like.

The procedures after the separation of the core-shell type metallic nanoparticles are carried out according to known processes. They are not particularly limited nor are they included in the scope of the present invention.

FIG. 1 is a schematic diagram showing the method according to the first aspect of the present invention, in which M denotes a nanoparticle of a first metal, M* denotes a second metal, and $M^*L_x$ denotes a metallic precursor containing the second metal. Referring to FIG. 1(a), it is shown that the particle M of the first metal and precursor containing the second metal $M^*L_x$ produce a core-shell type metallic nanoparticles $MM^*_c$ via transmetalation reaction. In other words, the particle M of the first metal forms into a core through intercohesion in order to reduce surface energy and the second metal M* forms around the core of the first metal via transmetalation reaction, thereby producing a core-shell structure.

By this method, core-shell structure having a uniform size can be obtained effectively, as shown in the Test Examples described below.

Also, according to the first aspect of the present invention, the present invention relates to a method for producing solid solution alloy type nanoparticles comprising (i) providing a solution of a thermally degradable metallic precursor A containing a first metal in an appropriate organic solvent; (ii) providing a solution of a metallic precursor B containing a second metal in an appropriate organic solvent, in which the second metal has a reduction potential higher than that of the first metal; and (iii) combining the solutions of the precursors A and B from (i) and (ii) together to carry out the transmetalation reaction of the first and second metals, thereby forming solid solution alloy type nanoparticles.

The first metal is not required to be limited to a specific metal as long as it has a reduction potential lower than that of the second metal. Preferably, the first metal may comprise a member selected from the group consisting of manganese, chromium, iron, cobalt, nickel, copper, silver, palladium, platinum and gold.

The metallic precursor A containing the first metal is not particularly limited as long as it can release the first metal as nanoparticles by thermal decomposing. Examples which satisfy the above requirements include carbonyl compounds such as $Co_2(CO)_8$, $Co_4$ $(CO)_{12}$, $Cr_2(CO)_7$, $Mn_2$ $(CO)_{10}$, $Fe(CO)_5$, $Fe_2(CO)_5$, $Fe_2(CO)_{10}$, $Ni(CO)_4$, etc.

The metallic precursor B containing the second metal is not particularly limited as long as it has a suitable composition for transmetalation with the first metal. Examples which satisfy the above requirements include β-diketonate compounds, phospine compounds, organic metallic compounds, hydrocarbonate ammonium salt compounds of $R_4N$, in which R is a straight or branched chain having 1 to 22 carbon atoms or a chain containing a phenyl group, and the like. The β-diketonate compounds may include, for example, $Pt(hfac)_2$ (hfac: hexafluoroacetylacetonate), $Au(hfac)$ $(PPh_3$: triphenylphospine), $Au(hfac$ $(PMe_3)$, $Me_2Au(hfac)$, $Me_2Au(tfac)$ (tfac:triflucroacetylacetonate), $Pd(hfac)_2$, $Au(acac)$ $(PPh_3)$ (acac; acetylacetonate), $Au(acac)$ $(PMe_3)$, $Ag(hfac)$, $Ag(hfac)$ $(PR_3)$, $Cu(hfac)_2$, $Pt(acac)_2$, $Pd(acac)_2$, $Ag(acac)$, $Ag(acac)$ $(PR_3)$, $Cu(acac)_{21}$ and the like, in which R is a straight or branched chain having 1 to 22 carbon atoms or a chain containing a phenyl group, and the like. The phospine compounds may include, for example, $Pt(PR_3)_4$, $AuCl(PPh_3)$, $Pd(PR_3)_4$, $[Ag(PR_3)I]_4$, $AuPR_3Cl$, $[(PR_3)_2]CuNo_3$, and the like, in which R is a straight or branched chain having 1 to 22 carbon atoms or a chain containing a phenyl group, and the like. The organic metallic compounds may include, for example, $Me_3AuPMe_3$, $EtAuPMe_3$, $Pt(COD)Cl_2$ (COD: cyclooctadiene), $Pt(COD)$ $(CH_3)_2$, $Pd(COD)Cl_2$, $Pd(COD)(CH_3)_2$, and the like. The hydrocarbonate ammonium salts $(R_4N)$ may include, for example, $[R_4N]AuCl_4$, $[R_4N]_2PtCl_4$, $[R_4N]_2PdCl_{41}$ $[R_4N]_2CuCl_4$, and the like, in which R is a straight or branched chain having 1 to 22 carbon atoms or a chain containing a phenyl group, and the like.

Now, the method for producing the solid solution alloy type nanoparticles will be described in detail.

Firstly, a metallic precursor A containing a first metal, as described above, is dissolved in an appropriate organic solvent to provide a solution of the precursor A.

Then, a metallic precursor B containing a second metal to be transmetalated with the first metal is dissolved in an appropriate organic solvent to provide a solution of the precursor B.

Preferably, upon preparing the solution of the precursor B containing the second metal, an appropriate stabilizer may be added to the solution so that the nanoparticles form a stable single dispersion phase in the solution. As the stabilizer, the same compounds as used in the method for producing the core-shell type metallic nanoparticles $MM^*_c$ and thus, the detailed explanation is omitted here.

Finally, in order to effectively carry out the transmetalation reaction, the solution of the precursor B is heated to a temperature between 50 arid 300° C., more preferably 120 to 150° C. To the heated solution of the precursor B, the solution of the precursor A is added and the temperature of the reaction was kept at the above-described temperature for 1 to 12 hours. At this time, it is preferable that the addition of the precursor A solution is quickly performed by injection means such as a syringe.

The separation of thusly obtained solid solution alloy type nanoparticles and subsequent processes are the same as described above and thus are omitted here.

Figure 2:
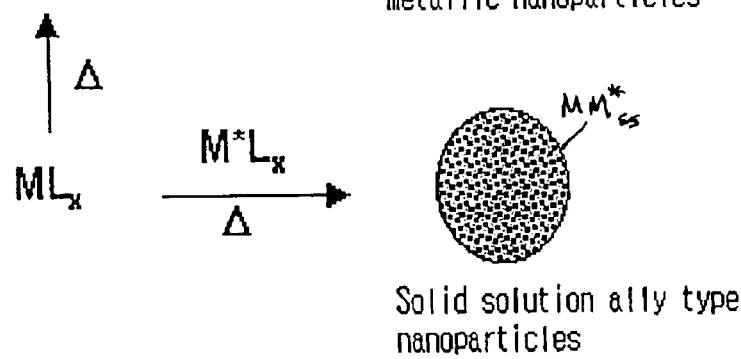

FIG. 2 is a schematic diagram of the method according to the second aspect of the present invention, in which M denotes a nanoparticle of a first metal, M* denotes a second metal, $ML_x$ denotes a metallic precursor A and $M^*L_x$ denotes a metallic precursor B. Referring to FIG. 1(b), it is shown that the metallic precursor containing the first metal A(MLx) and precursor containing the second metal $B(M^*L_x)$ produce solid solution alloy type nanoparticles $MM^*_{ss}$ via transmetalation reaction. In other words, the metallic precursor A generates a particle M of the first metal and at the same time, the metallic particles M is oxidation-reduction reacted with the solution of the metallic precursor B to form a metal M*, thereby producing a solid solution alloy type nanoparticle $MM^*_{ss}$.

By this method, solid solution alloy type nanoparticles having a uniform size can be obtained effectively, as shown in the Test Examples described below The core-shell type metallic nanoparticles $MM^*_c$ or the solid solution alloy type nanoparticles $MM^*_{ss}$ produced according to the present invention can find utilities in various industrial fields.

As an application of the present invention, there may be produced recording media for varieties of information using magnetic materials. The application can be realized by forming the nanoparticles produced according to the present invention into a thin layer on a given substrate by a known method. In this case, the usable substrate may include silicone, glass and sapphire substrate or any substrates or disks made of various metallic materials including aluminum which is used in the manufacture of platters in hard disks.

The method which can be used for forming the thin layer of the nanoparticles on the substrate includes known methods such as spin-coating (see Test Example 2), dip-coating and chemical magnetic assembly.

In order to manufacture a high density magnetic information storage device using metallic nanoparticles, very large coercive force is needed. The nanoparticles produced according to the present invention are stable in the air, as is described later (see Example 2 and FIG. 3d: in the X-ray diffraction analysis, the nanoparticles stored in the air does not show oxidation) and have strong corrosion-resistance (since platinum coated on the surface of cobalt has corrosion-resistance, the cobalt-platinum nanoparticles can withstand acid or base). Also, the nanoparticles have a large coercive force (see, Test Examples 1 and 2). Thus, if cobalt-platinum nanoparticles of 6 nm are aligned on a plane by self-assembling patterning method and one nanoparticle is used as one unit (bit) for storing information, next generation memory storage media having a recording density more than terabit ($10^{12}$) would be produced.

As a second application of the present invention, there may be produced information recording media which comprises a given substrate, a thin layer of a first metal coated on partial or entire surfaces of the substrate, and a transmetal layer formed over the thin layer of the first metal by selective chemical vapor deposition of a metallic precursor containing a second metal, in which the second metal has a reduction potential higher than that of the first metal. The coating of the first metal can be performed by known methods.

The information recording media having the above configuration is different from the information recording media of the first application which involves directly forming the core-shell type metallic nanoparticles on the substrate, in that the metallic precursor containing the second metal is deposited over the layer of the first metal nanoparticles thereby causing the transmetalation reaction to occur on the substrate (see, Test Example 3).

As a third application of the present invention, there may be provided chemical catalysts comprising as an active ingredient the metallic nanoparticles produced according to the present invention.

The metallic nanoparticles according to the present invention can be particularly used as a catalyst in chemical reactions such as reduction reaction of olefin (see: Test Example 4). Further, they can be provided as nucleation sites for production of carbon nanotubes.

The production of carton nanotubes can be carried out by the known vapor phase growth method. More particularly, the vapor phase growth is conducted by directly supplying reactant gases such as $C_2H_2$, $C_2H_4$, $CH_4$, $C_2H_6$ and a metallic catalyst to a reactor furnace to synthesize carbon nanotubes in gas phase. Therefore, this method is suggested to be advantageous in synthesizing the carbon nanotubes in mass. Since the metallic nanoparticles according to the present invention have a large surface area, the catalytic activity on the surface of metal would be excellent. Thus, they can be used as nucleation sites for production of carbon nanotubes.

As the fourth application of the present invention, there may be provided various medically effective therapeutic agents (including agents for diagnosis) comprising the metallic nanoparticles according to the present invention as an active ingredient. Specifically, the nanoparticles produced according to the present invention are bound to DNA or drugs. Then, the nanoparticles with DNA or drugs bound are attached to biomaterials of tumor cells or various body organs for use in tumor therapy, drug therapy and diagnoses of various diseases. Especially, gold coated magnetic nanoparticles of cobalt, iron, nickel can be used in the self-assembly and nano-patterning using gold nanoparticles, and also can be applied in many nanotechniques because of their capability to bind with biomaterials through various chemical bonds. Specific embodiments to which the nanoparticles according to the present invention are applicable can be achieved by known means and methods which are going on active research and studies, and explanation thereof would not be necessary.

As the fifth application of the present invention, there may be provided a single electron device comprising nanoparticles according to the present invention aligned between two electrodes so that the device has magnetic properties. As an example of the single electron device, there is a single electron transistor. Its specific embodiments are apparent to those skilled in the art and explanation thereof is omitted.

Now, the present invention will be described in detail with reference to following examples. These examples however, are intended to illustrate the present invention and should not be construed as limiting the scope of the present invention.

EXAMPLES—OVERVIEW

In the Examples, core-shell type metallic nanoparticles were prepared using cobalt as the first metal.

Preparation of Cobalt Nanoparticles

The cobalt nanoparticles were obtained from thermal decomposition of dicobaltoctacarbonyl ($Co_2(CO)_8$) Specifically, 0.44 g of bis-(2-ethylhexyl)sulphosuccinate (NaAOT) as a stabilizer was dissolved in toluene under nitrogen atmosphere The solution was heated to its boiling point of 110° C. Separately, 0.5 M of dicobeltoctacarbonyl dissolved in toluene was prepared. 4 ml of this solution was quickly injected to the boiling solution of the stabilizer. Consequently, brown colored dicobaltoctacarbonyl was thermally decomposed to form cobalt nanoparticles at a concentration of 0.1 M in a brownish black solution with evolution of Carbon monoxide gas (CO). The cobalt nanoparticles produced by this procedure had a particle size of about 6.33 nm. If needed, the particle size of the nanoparticles can be varied from 4 to 13 nm by adjusting the type and amount of the stabilizer, as shown in Table 1 below.

TABLE 1

| Stabilizer | Particle size (nm) |
| --- | --- |
| NaAOT 0.889 g | 4 |
| NaAOT 0.445 g | 6 |
| NaAOT 0.089 g | 8 |
| NaAOT 0.022 g + oleic acid 0.015 ml | 10 |
| NaAOT 0.011 g + oleic acid 0.015 ml | 13 |

Example 1

Preparation of Core-Shell Type Metallic Nanoparticles

In this example, the cobalt nanoparticles obtained from "Preparation of cobalt nanoparticles" method as described above in paragraph 59, were used as the first metal. The cobalt nanoparticles were dissolved in 40 ml of nonane to make a 0.1 M solution. Separately, 0.14 g of Pt(hfac)2 and 0.06 ml of dodecylisocyanate were added to 5 ml of nonane. To this solution, 5 ml of the previously prepared nonane solution of cobalt was added and heated to 150° C. for B hours.

The solution was cooled to room temperature. Ethanol was added thereto arid centrifuged at 3000 RPM for 20 minutes to separate precipitates.

Figure 3A:
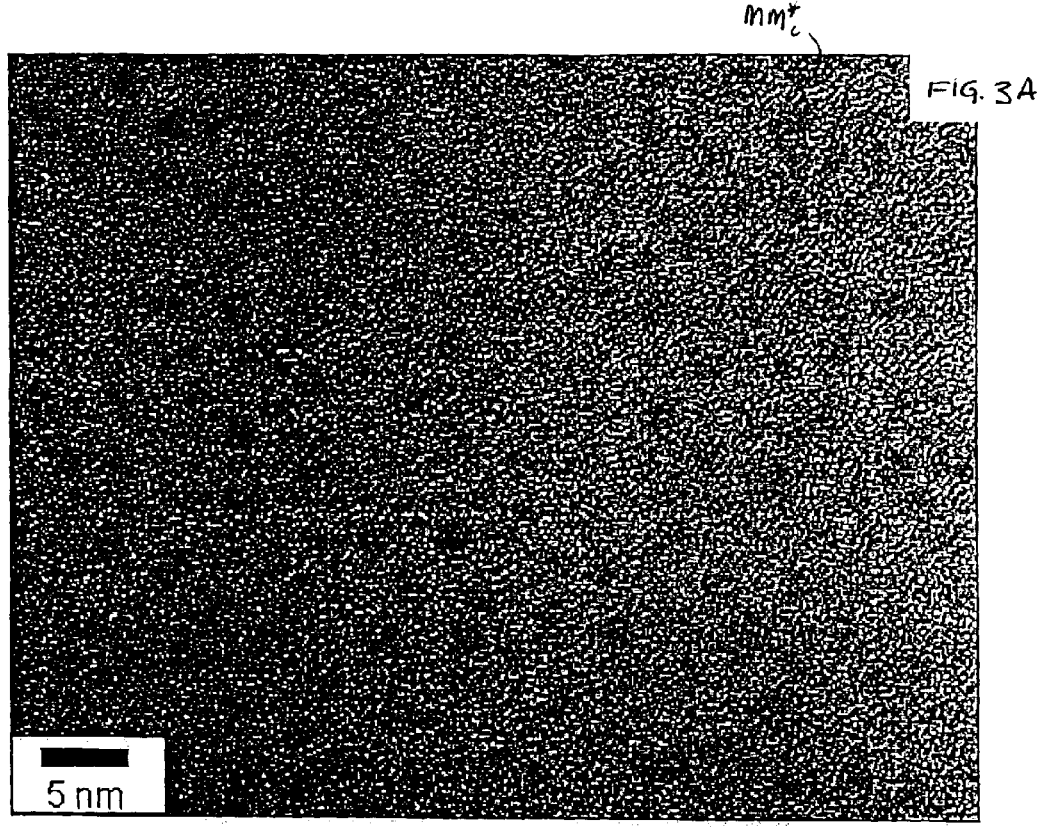
FIGS. 3A and 3B shows a photograph from a transmission electron microscope (TEM) of core-shell type cobalt-platinum nanoparticles produced according to present invention.
Figure 3B:
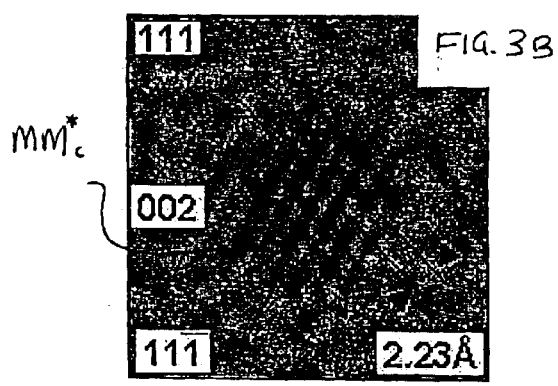

FIG. 3A shows a photograph, taken using EM912 Omega, a transmission electron microscope (TEM) at electron beam of 120 KV, of the core-shell type cobalt-platinum nanoparticles MM*$_c$ produced according to this example. FIG. 3B shows a photograph, taken using Hitachi H9000-NAR, a high resolution TEM at electron beam of 300 KV, for the core-shell type cobalt-platinum nanoparticles MM*$_c$ produced according to this example.

Figure 4:
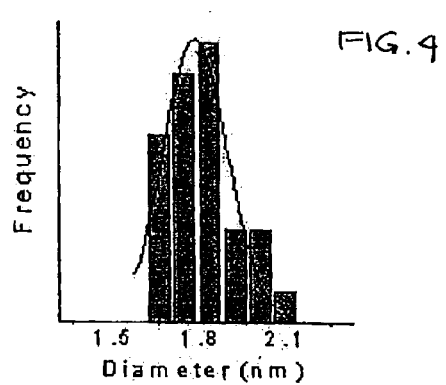
FIG. 4 Shows a size distribution chart of the size of the nanoparticles.

In the picture of FIG. 3A, each black circle represent one core-shell type cobalt-platinum nanoparticle MM*$_c$. As shown in FIG. 4, which is a size distribution chart, the nanoparticles have a uniform size distribution within 10%.

Particularly, according to the picture from the high resolution transmission electron microscope in FIG. 3B, the lattice spacing of the shell is 2.27 Å. This value approximates 2.265 Å, which is the spacing between planes of platinum, which shows that the shell of the nanoparticles are well coated with platinum. In addition, as seen from FIG. 4a showing results of energy dispersive X-ray analysis the ratio of cobalt to platinum was found to be 45:55. Therefore, it is confirmed, that the cobalt arid platinum are contained in the composition at a ratio of 1:1 via transmetalation reaction.

Example 2

Preparation of solid solution alloy type nanoparticles 0.25 g of Pt(hfac)$_2$ and 0.1 ml of oleic acid were added to 5 ml of toluene and boiled. 5 ml of 0.5 M solution of dicobaltoctacarhonyl in toluene was added thereto and boiled for 12 hours.

The solution was cooled to room temperature. Ethanol was added thereto and centrifuged at 3000 RPM for 20 minutes to separate precipitates.

Figure 5:
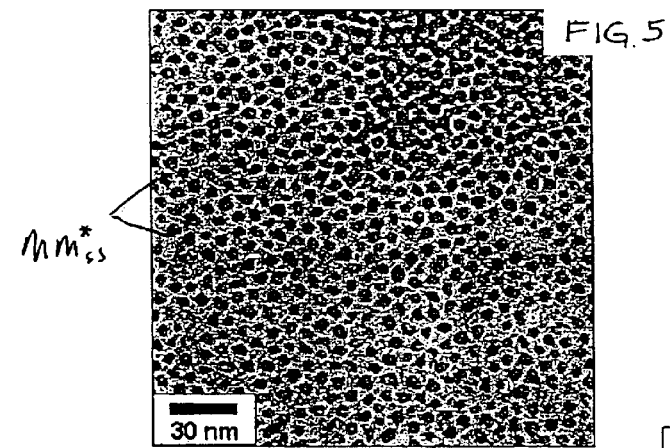
FIG. 5 shows a photograph from a transmission electron microscope (TEM)
Figure 6:
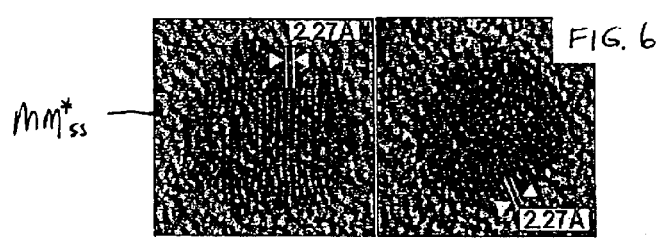
FIG. 6 is an enlargement of FIG. 5.

FIG. 5 shows a photograph, taken using EM912 Omega, a transmission electron microscope (TEM) at electron beam of 120 KV of the solid solution alloy type cobalt-platinum nanoparticles MM*$_{ss}$ produced according to this example. FIG. 6 shows a photograph, taken using a Hitachi H9000-NAR, a high resolution TEM at electron beam of 300 KV of the solid solution alloy type cobalt-platinum nanoparticles MM*$_{ss}$ produced according to this example.

Figure 7:
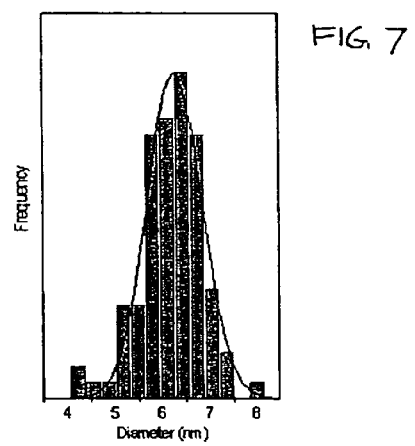
FIG. 7 is a size distribution chart.

In the TEM picture of FIG. 5, it was confirmed that the produced cobalt-platinum nanoparticles were of solid solution alloy type and had a particle size of 1.8 nm. As shown in FIG. 7 which is a size distribution chart, the nanoparticles have a uniform size distribution within 10%.

Figure 8:
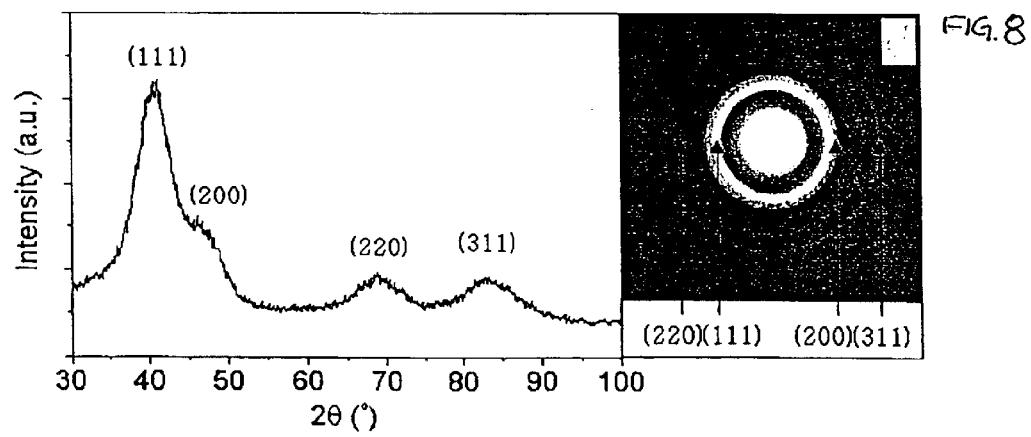
FIG. 8 shows as X-ray diffraction analysis and electron beam diffraction analysis for solid solution alloy type cobalt-platinum nanoparticles produced according to the present invention.
Figure 9:
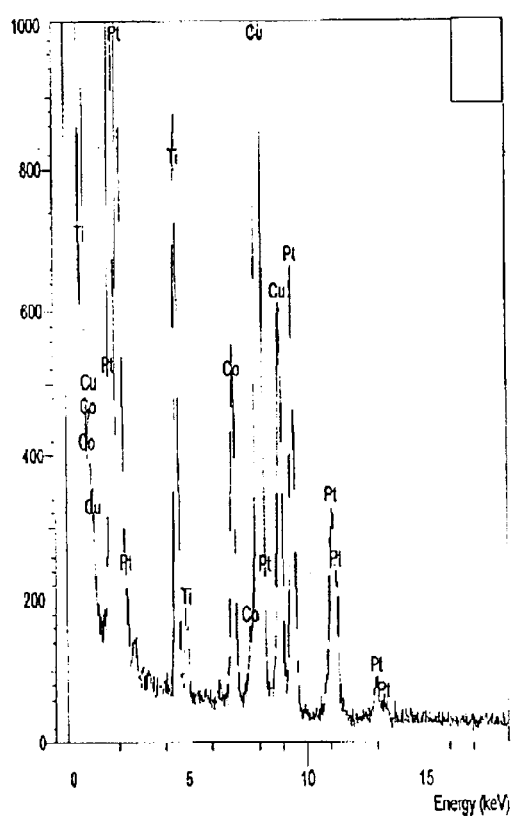
FIGS. 9 and 10 show results of energy dispersive X-ray analyses for core-shell type cobalt-platinum nanoparticles produced according to the present invention and solid solution alloy type cobalt-platinum nanoparticles produced according to the present invention, respectively.
Figure 10:
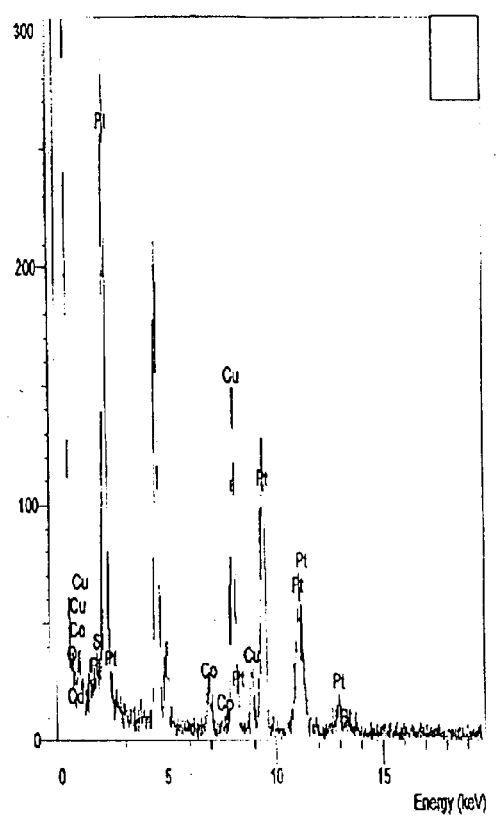

Particularly, according to the picture from the high resolution transmission electron microscope in FIG. 6, the lattice spacing of the shell is 2.23 Å. This approximates to 2.227 Å, which is the spacing between planes of regular hexagonal $CoPt_3$. Thus, it can be confirmed that the nanoparticles are well formed solid solution alloy type cobalt-platinum nanoparticles. In addition, as seen from FIG. 10 showing results of energy dispersive X-ray analysis, composition ratio of cobalt to platinum of the produced nanoparticles was found to be 23:77, i.e. 1:3. Further, as a result of X-ray diffraction analysis, the nanoparticles configuration accords with the regular hexagonal configuration of $CoPt_3$ (FIG. 8).

Test Example 1

Measurement of Coercive Force

Figure 11:
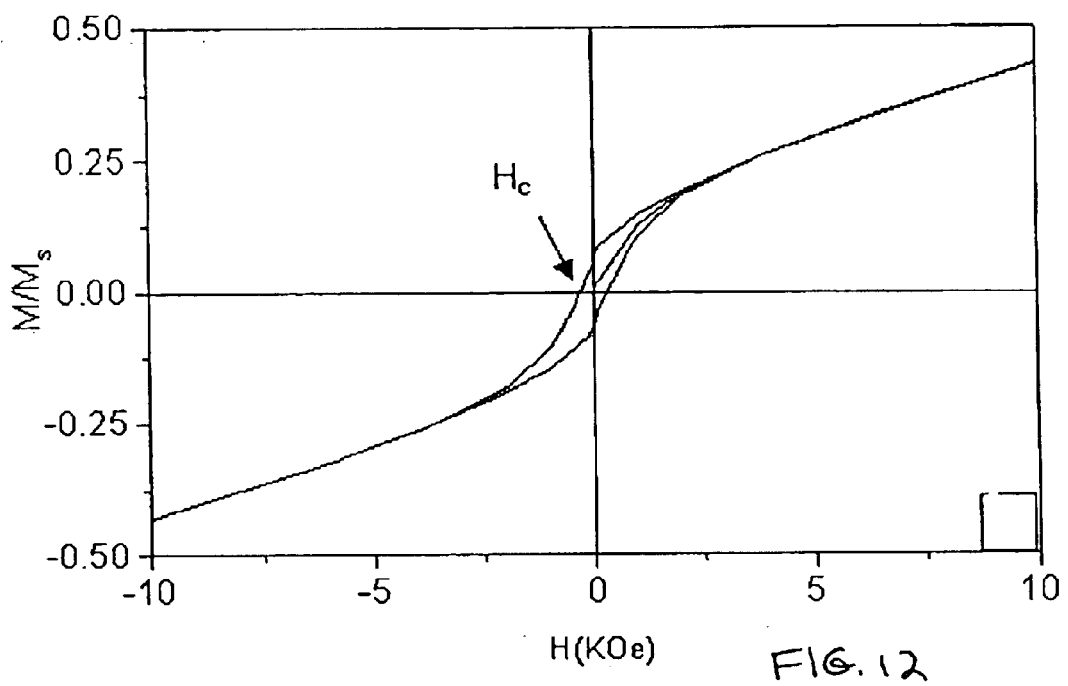
FIGS. 11 and 12 show magnetic hysteresis loops at 5K of core-shell type cobalt-platinum nanoparticles produced according to the present invention and solid solution alloy type cobalt-platinum nanoparticles produced according to the present invention, respectively, in which the core-shell type cobalt-platinum nanoparticles have a coercive force of 330 Oe in FIG. 5a and the solid solution alloy type cobalt-platinum nanoparticles have a coercive force of 6900 Oe.
Figure 12:
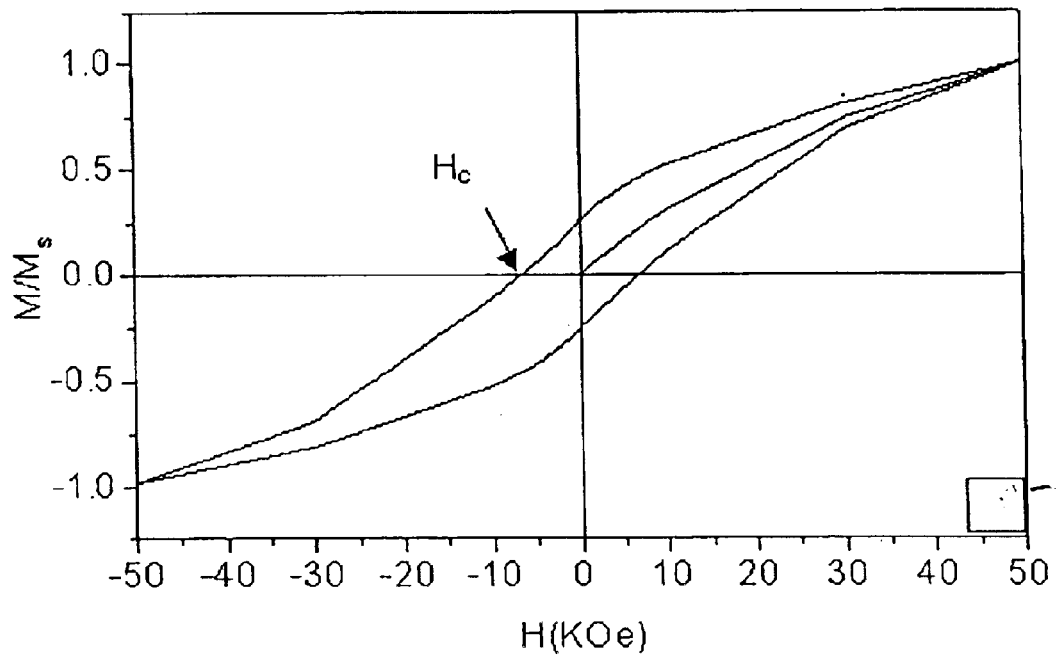

The cobalt-platinum nanoparticles prepared in Examples 1 and 2 were measured for their magnetic properties using SQUID (Superconducting Quantum Interference Device, quantum design MPMS 7). FIG. 11 shows a magnetic hysteresis loop at 5K of the core-shell type cobalt-platinum metallic nanoparticles prepared in Example 1. From the loop it was found that the coercive force of the nanoparticles was 330 Oe. FIG. 12 shows a magnetic hysteresis loop at 5K of the solid solution alloy type cobalt-platinum alloy nanoparticles prepared in Example 2. From the loop it was found that the coercive force of the nanoparticles was 6900 Oe.

The nanoparticles were found to have super-paramagnetic properties not showing magnetic hysteresis at room temperature of 300 K.

Test Example 2

Preparation of a Thin Layer by Spin Coating and Measurement of Coercive Force

Figure 13:
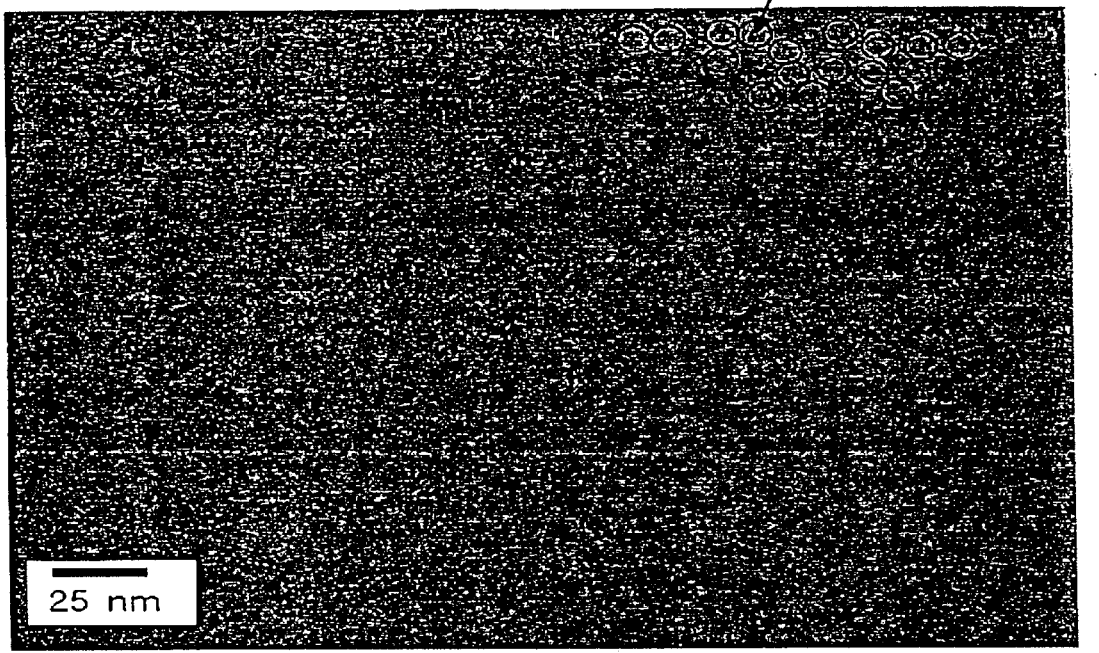
FIG. 13 shows a photograph from a scanning electron microscope (SEM) of core-shell type cobalt-platinum nanoparticles produced according to the present invention spin-coated on a silicone substrate.

Respective core-shell type and solid solution alloy type cobalt-platinum nanoparticles were dispersed in toluene and spin coated at 5000 rpm for 60 seconds to form a uniform thin layer of nanoparticles as shown in FIG. 13. The magnetic thin layer of the core-shell type cobalt-platinum nanoparticles was heat treated at 700° C. for 12 hours. The resulting thin layer showed a great coercive force of 5300 Oe at room temperature as shown in FIG. 14A.

Test Example 3

Figure 15:
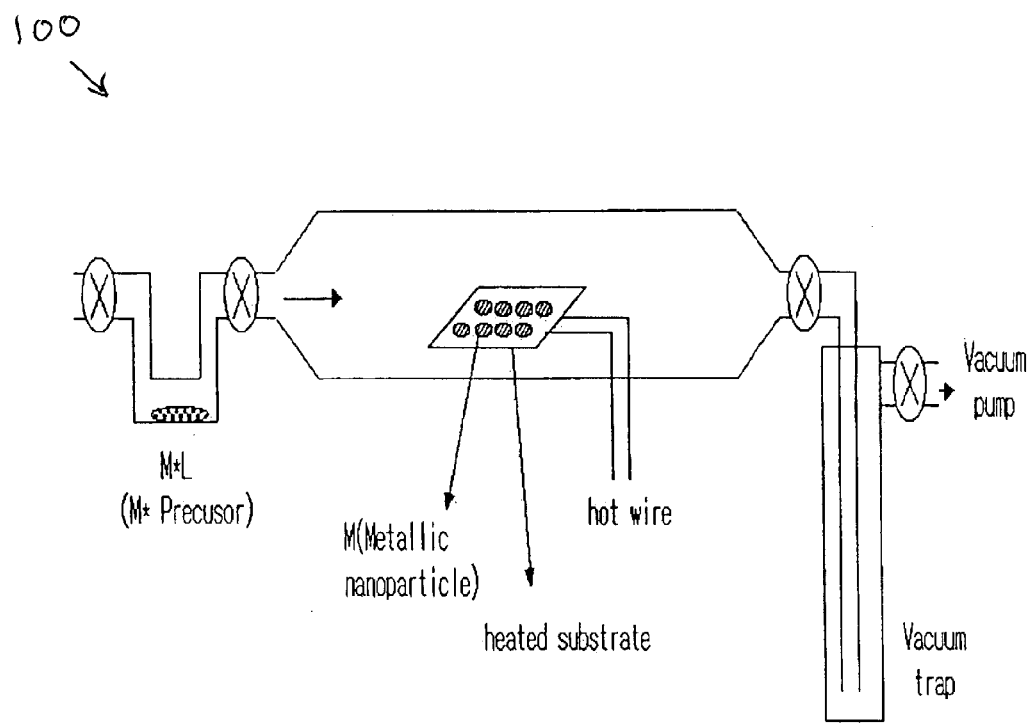
FIG. 15 shows a schematic view of selective chemical vapor deposition (CVD) apparatus for conducting the transmetalation ion reaction.
Figure 16:
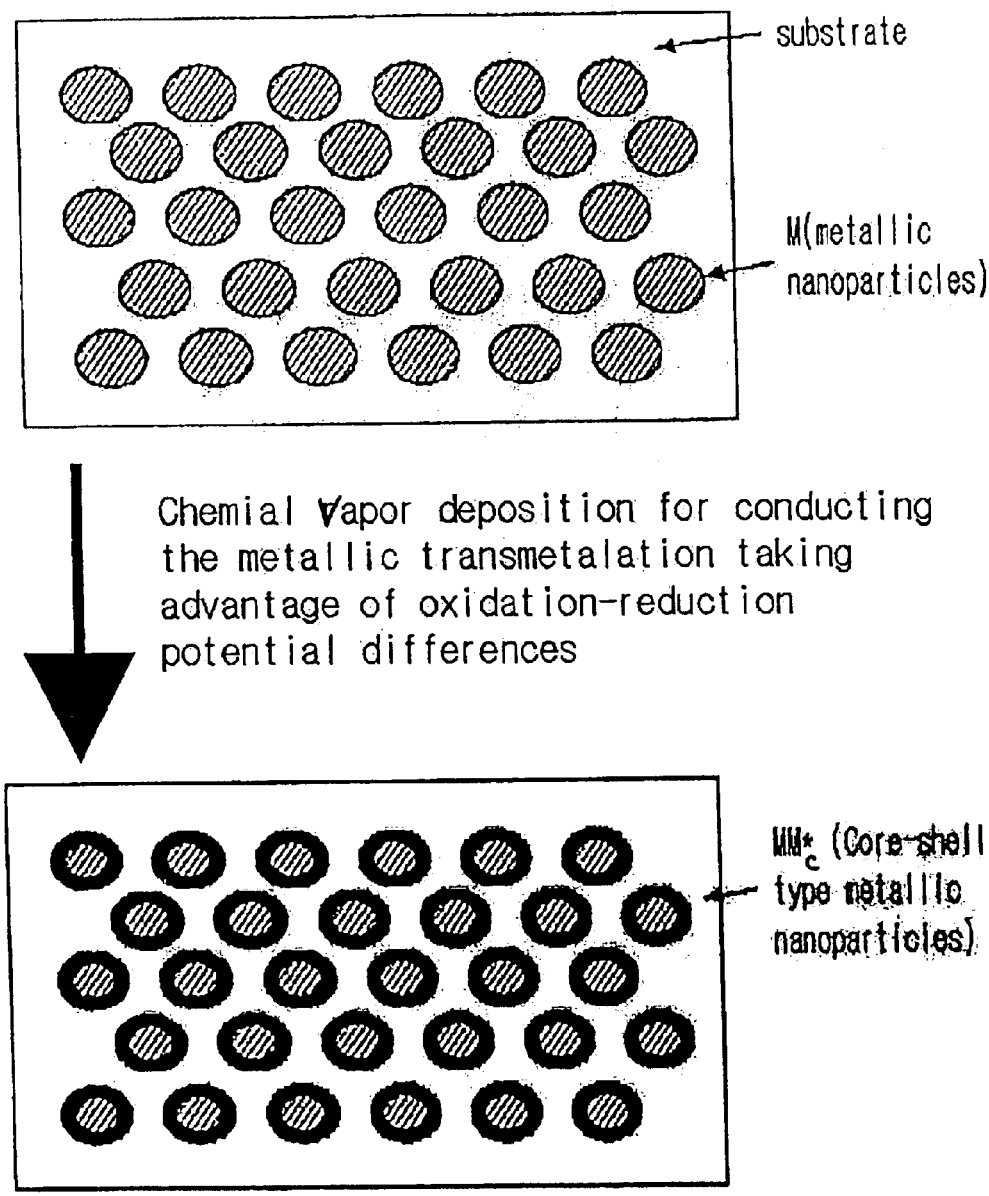
FIG. 16 shows a schematic view of the process for selectively and chemically vapor depositing metallic precursor capable of transmetalating to metallic nanoparticles and nanorods spin-coated on a silicone substrate, thereby forming alloys.

Preparation of a Cobalt-Platinum Nanoparticles Layer by Chemical Vapor Deposition FIG. 15 shows a schematic view of a selective chemical vapor deposition (CVD) apparatus 100 for conducting the transmetalation reaction, and FIG. 16 shows a schematic view of the process for selectively and chemically vapor depositing metallic precursor capable of transmetalating to metallic nanoparticles and nanorods spin-coated on a silicone substrate.

Figure 17:
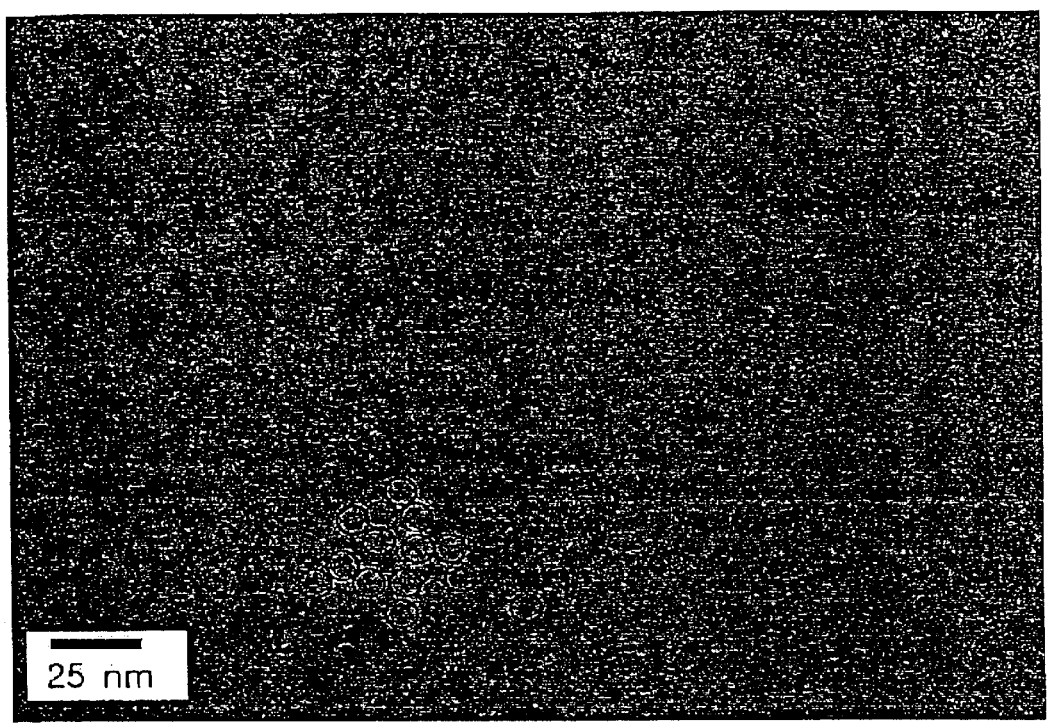
FIG. 17 shows a photograph from a scanning electron microscope (SEM) of core-shell type cobalt-platinum nanoparticles which are produced by selectively and chemically vapor depositing platinum using $Pt(hfac)_2$ which is a metallic precursor capable of transmetalating to cobalt nanoparticles spin-coated on a silicone substrate.

Using the CVD apparatus 100, the cobalt nanoparticles prepared as in the "Preparation of cobalt nanoparticles" section which is detailed above, were dispersed in toluene and spin coated on a silicone substrate. Subsequently, Pt(hfac)$_2$, the precursor containing the second metal was deposited by chemical vapor deposition over the silicon substrate having the cobalt nanoparticles coated thereon. The platinum was transmatalated selectively to the nanoparticles of cobalt to form a core-shell type cobalt-platinum nanoparticles, as shown in FIG. 17.

Test Example 4

Reduction of Olefin

The cobalt-platinum nanoparticles prepared in Example 1 were used as a catalyst for reduction of olefin.

The cobalt-platinum nanoparticles were dispersed in tetrahydrofuran, followed by addition of olefinic compound such as 1,3-cyclooctadiene. The dispersion was left at room temperature and hydrogen pressure of 1 atm to obtain cyclooctene as a reduced product.

As described above, according to the present invention, it is possible to produce core-shell type metallic nanoparticles or solid solution alloy type nanoparticles from any heterogeneous metals capable of transmetalating. Since the nanoparticles produced in this way are excellent in physical and chemical stability and uniformity, they are expected to be applicable to various industrial fields including new information recording media.

While there have been illustrated and described what are considered to be preferred specific embodiments of the present invention, it will be understood by those skilled in the art that the present invention is not limited to the specific embodiments thereof, and various changes and modifications and equivalents may be substituted for elements thereof without departing from the true scope of the present invention.

What is claimed is:

1. A method for producing core-shell type metallic alloy nanoparticles, comprising:

providing a dispersion of a first metal as nanoparticles in an appropriate organic solvent;

providing a solution of a metallic precursor containing a second metal in an appropriate organic solvent, in which the second metal has a reduction potential higher than that of the first metal; and combining the dispersion and the solution together to carry out the transmetalation reaction of the first and second metals, thereby core-shell type metallic alloy nanoparticles are formed.

2. The method according to claim 1, wherein a stabilizer is added to the solution of the metallic precursor containing the second metal.

3. The method according to claim 2, wherein the stabilizer includes compounds having following structures:

R—X in which R is a straight or branched hydrocarbonate group having 2 to 22 carbon atoms and X is selected from a isocyanate group, sulphonate group, phosphate group, carboxylate group, amine group and thiol group.

4. The method according to claim 1, wherein the first metal comprises a member selected from the group consisting of manganese, chromium, iron, cobalt, nickel, copper, silver, palladium, and platinum.

5. The method according to claim 1, wherein the first metal comprises at least two metals in the form of core-shell type metallic nanoparticles.

6. The method according to claim 1, wherein the metallic precursor containing the second metal comprises at least one member selected from the group consisting of β-diketonate compounds, phospine compounds, organic metallic compounds, hydrocarbonate ammonium salt compounds of R$_4$N, in which R is a straight or branched chain having 1 to 22 carbon atoms or a chain containing a phenyl group.

7. The method according to claim 1, wherein the reaction temperature required for the transmetalation reactions is 50 to 300° C.

* * * * *